US00PP32420P2

(12) United States Plant Patent
van Meuwen et al.

(10) Patent No.: US PP32,420 P2
(45) Date of Patent: Nov. 3, 2020

(54) ***ACER* PALMATUM TREE NAMED 'ARJOS1'**

(50) Latin Name: *Acer palmatum*
Varietal Denomination: ARJOS1

(71) Applicants: Johannes Marinus van Meuwen, Waddinxveen (NL); Arie Jacobus Keijzer, Boskoop (NL)

(72) Inventors: Johannes Marinus van Meuwen, Waddinxveen (NL); Arie Jacobus Keijzer, Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/501,676

(22) Filed: May 21, 2019

(51) Int. Cl.
*A01H 5/00* (2018.01)
*A01H 6/00* (2018.01)

(52) U.S. Cl.
USPC ..... Plt./224

(58) Field of Classification Search
USPC ..... Plt./224
See application file for complete search history.

(56) References Cited

PUBLICATIONS

UPOV: PLUTO Plant Variety Database Mar. 2, 2020 retrieved from the Internet at <https://www3.wipo.int/pluto/user/en/index.jsp> cultivar name 'ARJOS1', (one page).*

* cited by examiner

*Primary Examiner* — Susan McCormick Ewoldt
(74) *Attorney, Agent, or Firm* — Cassandra Bright

(57) ABSTRACT

A new and distinct *Acer palmatum dissectum* tree named 'ARJOS1' is disclosed, characterized by young foliage colored yellow green with pink-red margins turning to white and green leaves. Trees have an outwardly spreading, arching habit. Fall color is purple-red. The new variety is a dwarf tree, typically used for outdoor garden or container use.

2 Drawing Sheets

Figure 1:
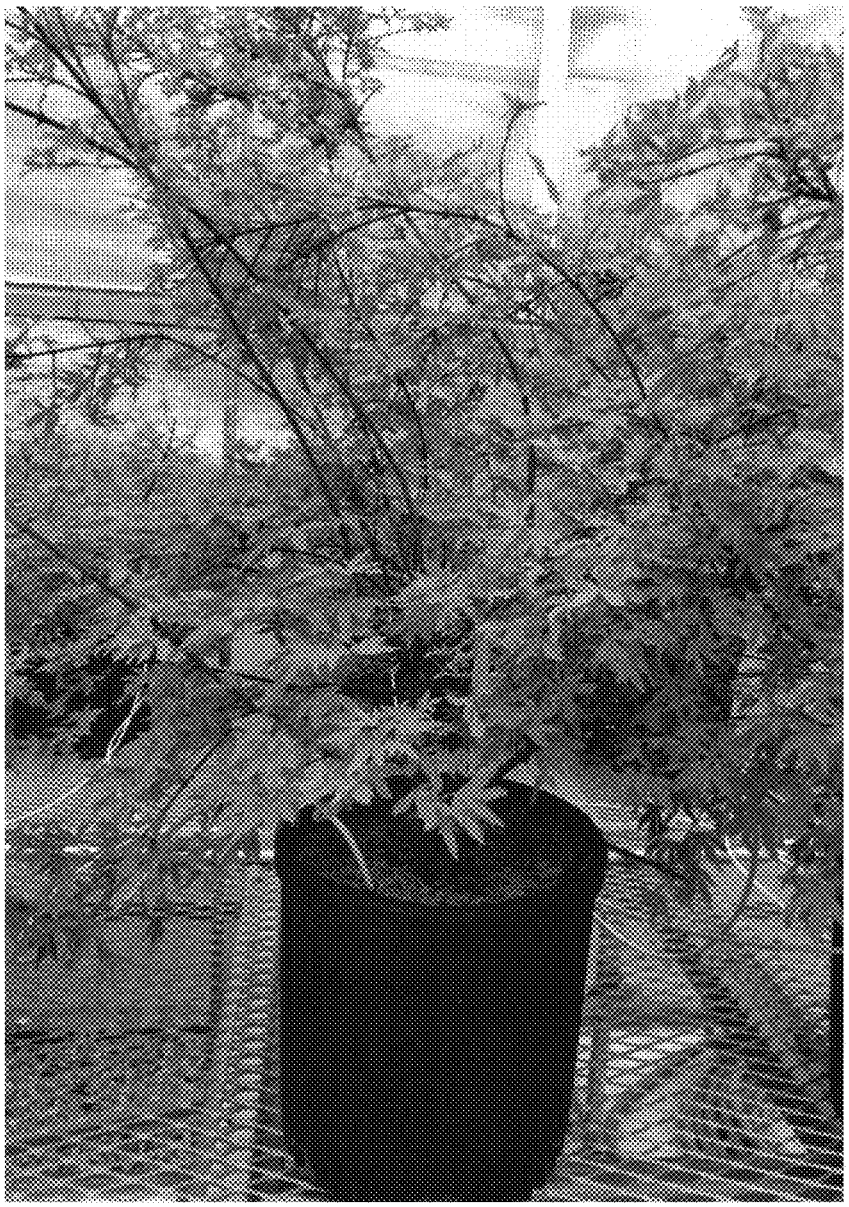

Latin name of the genus and species: *Acer palmatum.*
Variety denomination: 'ARJOS1'.

BACKGROUND OF THE INVENTION

The new cultivar is a product of chance discovery. The new variety was discovered as a naturally occurring single branch mutation of *Acer palmatum* 'Orange Dream', unpatented. The inventors discovered this interesting mutation in April of 2001 at a commercial nursery in Waddinxveen, the Netherlands.

Asexual reproduction of the new cultivar 'ARJOS1' was first performed during May of 2001at a commercial nursery in Waddinxveen, the Netherlands. Semi-softwood cuttings of the new variety were rooted. Subsequent propagation has shown that the unique features of this cultivar are stable and have been reproduced true to type for five successive generations. First public access to plants of the variety occurred May 22, 2018 in the United Kingdom. This access came directly or indirectly from the inventor, qualifying for the exception allowed under 102(b). Previous to this public access, although the variety may have been publicized in print, plants were not available to the public for propagation.

SUMMARY OF THE INVENTION

The cultivar 'ARJOS1' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ARJOS1' grown in Dayton, Oreg. These characteristics in combination distinguish 'ARJOS1' as a new and distinct *Acer palmatum* cultivar:

1. Young foliage is yellow green with pink-red margins turning to white and green leaves.
2. White and green variegated leaves turn to purple-red fall color.
3. Spreading and arching growth habit.

PARENT COMPARISON

Plants of the new cultivar 'ARJOS1' are similar to plants of the parent *Acer palmatum* 'Orange Dream' in most horticultural characteristics, however, plants of the new cultivar 'ARJOS1' differ in the following;

1. New foliage of the comparator is white and green variegated, new foliage of the new variety is yellow-green with pink-red margins.
2. 'Orange Dream' has Fall foliage colored yellow-brown, Fall foliage of 'ARJOS1' is purple-red.

COMMERCIAL COMPARISON

Plants of the new cultivar 'ARJOS1' are similar to plants of *Acer palmatum* 'Butterfly', unpatented, in most horticultural characteristics, however, plants of the new cultivar 'ARJOS1' differ in the following;

1. The new variety produces foliage which is yellow-green with a white margin, foliage of 'Butterfly' is a darker green with a white margin.
2. Plant habit of 'ARJOS1', spreading and arching over, plant habit of 'Butterfly' is more upright.

Plants of the new cultivar 'ARJOS1' are similar to plants of the unpatented commercial variety, *Acer palmatum* 'Seiryu' in most horticultural characteristics, however, plants of the new cultivar 'ARJOS1' differ in the following;

1. The new variety produces foliage which is yellow-green with a white margin, foliage of 'Seiryu' is solid green.
2. Plant habit of 'ARJOS1', spreading and arching over, plant habit of 'Seiryu' is more upright.

BRIEF DESCRIPTION OF THE PHOTOGRAPHS

The accompanying photograph in FIG. 1 illustrates a tree in a 3 gallon pot.

Figure 2:
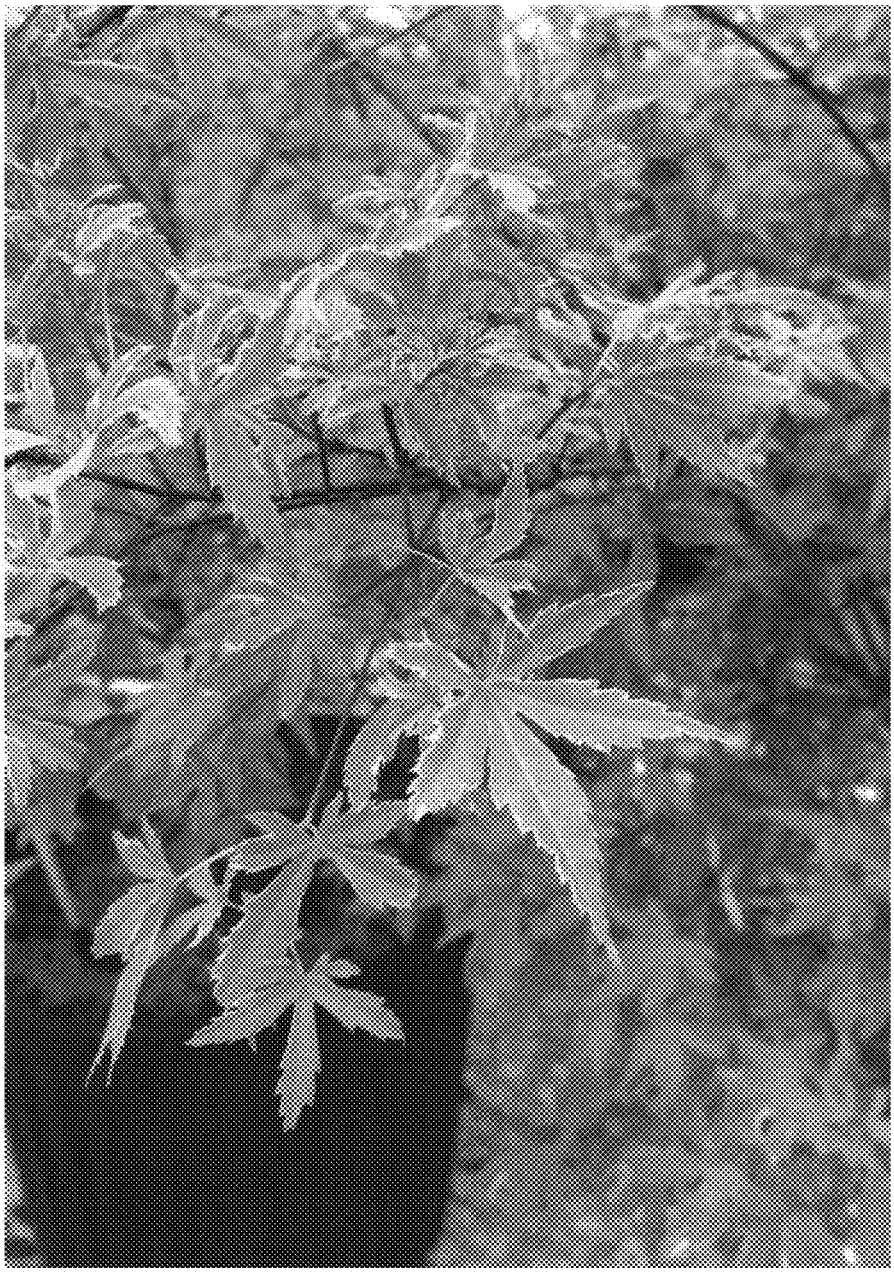

FIG. 2 illustrates a close up view of typical mature foliage of 'ARJOS1'. Trees are approximately 2 years old.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'ARJOS1' plants grown outdoors and in a nursery in Grand Haven, Mich. Plants are approximately 2 to 3 years old, in a 3 gallon nursery container. Temperatures ranged from 5° C. to 10° C. at night to 18° C. to 27° C. during the day. Measurements and numerical values represent averages of typical plant types.

Botanical classification: *Acer palmatum* 'ARJOS1'.

PROPAGATION

Time to initiate roots: About 50 to 60 days at approximately 25° C.

Root description: Fibrous. Fine, brown roots not accurately measured with an RHS chart.

PLANT

Growth habit: Outwardly spreading, arching, deciduous small tree with moderate vigor.

Pot Size of described plant: 3 gallon.

Height: 53 cm.

Plant spread: 114 cm.

Branch internode length: 3 to 4 cm.

Lateral branch characteristics:

*Quantity.*—Average range 7 to 15.

*Length.*—Average 80 cm.

*Diameter.*—7 mm.

*Texture.*—Smooth.

*Aspect and angle.*—Straight, outward about 75° from vertical.

*Color.*—Near RHS Yellow-Green 152B.

Trunk characteristics:

*Diameter.*—About 3.0 cm.

*Color.*—Near RHS Yellow-Green 152B.

*Texture.*—Smooth.

FOLIAGE

Leaf:

*Arrangement.*—Opposite.

*Average length.*—Approximately 2 to 4 cm.

*Average width.*—Approximately 3.5 to 5.5 cm.

*Shape of blade.*—Palmately lobed.

*Apex.*—Acute.

*Base.*—Truncate.

*Margin.*—Serrate.

*Texture of top surface.*—Leathery with slightly raised veins.

*Texture of lower surface.*—Leathery with raised veins.

*Leaf internode length.*—Average range 1.0 to 2.0 cm.

*Color.*—Young foliage: Upper side: Near RHS Yellow-Green N144C with Greyed-Purple 185D margins. Under side: Near RHS Yellow-Green N144C with Greyed-Purple 185D margins. Mature foliage: Upper side: Near RHS Yellow-Green N144A with Green-White 157C margins. Under side: Near RHS Yellow-Green N144A with Green-White 157C margins. Mature Fall foliage: Upper side: Near Greyed-Purple 185B, margin flushed 187B. Under side: Near Greyed-Purple 184B.

*Venation.*—Type: Palmate. Color: Venation color upper side: Near RHS Yellow-Green 144C. Venation color under side: Near RHS Yellow-Green 144C. Petiole: Length: Average 2.0 cm. Diameter: Average 0.1 cm. Color: Upper side: Near RHS Yellow-Green 144D. Under side: Near RHS Yellow-Green 144D.

FLOWER

Flowering not observed to date.

OTHER CHARACTERISTICS

Disease/pest resistance: Neither resistance nor susceptibility to normal diseases and pests of *Acer* has been observed.

Drought resistance: No tolerance for drought.

Temperature tolerance: USDA Zones 4 through 8.

What is claimed is:

1. A new and distinct cultivar of *Acer palmatum* dissectum tree named 'ARJOS1' as herein illustrated and described.

* * * * *